United States Patent
Tadic et al.

(10) Patent No.: US 11,478,355 B2
(45) Date of Patent: Oct. 25, 2022

(54) IMPLANT FOR COVERING BONE DEFECTS IN THE JAW REGION AND METHOD FOR PRODUCING THE SAME

(71) Applicant: Botiss Biomaterials GmbH, Zossen (DE)

(72) Inventors: Drazen Tadic, Berlin (DE); Oliver Bielenstein, Berlin (DE)

(73) Assignee: Botiss Biomaterials GmbH, Zossen (DE)

(*) Notice: Subject to any disclaimer, the term of this patent is extended or adjusted under 35 U.S.C. 154(b) by 0 days.

(21) Appl. No.: 15/551,217

(22) PCT Filed: Dec. 3, 2015

(86) PCT No.: PCT/EP2015/078499
§ 371 (c)(1),
(2) Date: Aug. 15, 2017

(87) PCT Pub. No.: WO2016/134797
PCT Pub. Date: Sep. 1, 2016

(65) Prior Publication Data
US 2018/0036127 A1 Feb. 8, 2018

(30) Foreign Application Priority Data

Feb. 24, 2015 (DE) .................. 102015102597.3

(51) Int. Cl.
*A61F 2/28* (2006.01)
*A61L 31/14* (2006.01)
*A61L 31/08* (2006.01)
*A61C 8/00* (2006.01)

(52) U.S. Cl.
CPC .......... *A61F 2/2803* (2013.01); *A61C 8/0092* (2013.01); *A61L 31/088* (2013.01); *A61L 31/14* (2013.01); *A61L 31/148* (2013.01); *A61F 2240/00* (2013.01);
(Continued)

(58) Field of Classification Search
CPC ......... A61F 2/2803; A61F 2310/00041; A61B 17/8071; A61C 8/0031; A61C 8/0039
See application file for complete search history.

(56) References Cited

U.S. PATENT DOCUMENTS 5,397,235 A * 3/1995 Elia .......................... A61C 8/00
433/173
5,511,565 A * 4/1996 Syers ................. A61B 17/8071
128/859
(Continued)

FOREIGN PATENT DOCUMENTS

CN 102170921 A 8/2011
CN 102206819 A 10/2011
(Continued)

OTHER PUBLICATIONS

Translation of JP2010082146 retrieved from espacenet on Feb. 12, 2019 (Year: 2019).*
(Continued)

*Primary Examiner* — Megan Y Wolf
(74) *Attorney, Agent, or Firm* — Smartpat PLC

(57) ABSTRACT

The invention relates to an implant for covering bone defects in the jaw region, which comprises a magnesium film.

19 Claims, 6 Drawing Sheets

(52) U.S. Cl.
CPC ............... *A61F 2310/00017* (2013.01); *A61F 2310/00041* (2013.01); *A61L 2430/02* (2013.01)

(56) References Cited

U.S. PATENT DOCUMENTS

| | | | | |
|---|---|---|---|---|
| 5,980,252 | A * | 11/1999 | Samchukov | A61C 8/0006 433/172 |
| 6,391,059 | B1 * | 5/2002 | Lemperle | A61B 17/688 606/151 |
| 2006/0136071 | A1 * | 6/2006 | Maspero | A61L 27/56 623/23.76 |
| 2006/0287732 | A1 * | 12/2006 | Pezeshkian | A61C 8/0092 623/17.17 |
| 2007/0042326 | A1 * | 2/2007 | Cardoso | A61C 8/0006 433/229 |
| 2008/0131479 | A1 | 6/2008 | Weber et al. | |
| 2009/0081313 | A1 | 3/2009 | Aghion et al. | |
| 2010/0036429 | A1 | 2/2010 | Buck | |
| 2010/0215718 | A1 * | 8/2010 | Swords | A61L 27/227 424/423 |
| 2010/0256773 | A1 * | 10/2010 | Thijs | A61F 2/2803 623/23.55 |
| 2011/0035024 | A1 * | 2/2011 | Malmquist | A61F 2/2803 623/23.72 |
| 2011/0098724 | A1 | 4/2011 | Cichocki et al. | |
| 2011/0313527 | A1 | 12/2011 | Witte et al. | |
| 2013/0274819 | A1 | 10/2013 | Horvath | |
| 2013/0304134 | A1 | 11/2013 | Tamai et al. | |
| 2016/0183990 | A1 * | 6/2016 | Koizumi | A61C 8/0006 606/285 |

FOREIGN PATENT DOCUMENTS

| | | | | |
|---|---|---|---|---|
| CN | 203328788 | U | 12/2013 | |
| DE | 102006011348 | A1 * | 9/2007 | ............ A61L 27/306 |
| DE | 102006011348 | A1 | 9/2007 | |
| DE | 102008037204 | A1 | 2/2010 | |
| DE | 102010055432 | A1 | 6/2012 | |
| JP | 2009-535504 | A | 10/2009 | |
| JP | 2009-545407 | A | 12/2009 | |
| JP | 2010082146 | A * | 4/2010 | |
| JP | 2010082146 | A | 5/2010 | |
| JP | 2011136967 | A | 7/2011 | |
| JP | 2012-102205 | A1 | 6/2014 | |
| RU | 2012121827 | A | 12/2013 | |
| WO | 2015185597 | A2 | 12/2015 | |
| WO | WO-2015185597 | A2 * | 12/2015 | ............ A61L 27/58 |

OTHER PUBLICATIONS

Translation of WO2015/185597A2 retrieved from espacenet on Apr. 29, 2019 (Year: 2019).*
Translation of DE102006011348A1 retrieved from espacenet on Apr. 29, 2019 (Year: 2019).*
Japanese Office Action dated Dec. 25, 2018 in counterpart JP Patent Application No. 2017-545660.
Officer Nora Lindner, "Translation of International Preliminary Report on Patentability and the Written Opinion", International Patent Application PCT/EP2015/078499, dated Sep. 29, 2017, 10 pp.
Officer: Werner Hubner, "International Search Report and the Written Opinion", International Patent Application No. PCT/EP2015/078499, Completed Jan. 26, 2016, 13 pp.
Dr. Jurgen Seidl, "German Office Action", German Patent Application No. 102015102597.3, dated Sep. 16, 2015, 15 pp.
Ian Johnson et al: "A Study on Factors Affecting the Degradation of Magnesium and a Magnesium-yttrium Alloy for Biomedical Applications", p. e65603, PLoS ONE 8(6): e65603. https://doi.org/10.1371/journal.pone.0065603, Jun. 14, 2013 (Jun. 14, 2013).
Liu J, Kerns DG. Mechanisms of guided bone regeneration: a review. Open Dent J. 2014;8:56-65. Published May 16, 2014. doi:10.2174/1874210601408010056.

* cited by examiner

IMPLANT FOR COVERING BONE DEFECTS IN THE JAW REGION AND METHOD FOR PRODUCING THE SAME

FIELD OF THE INVENTION

The invention relates to a bioresorbable implant for covering bone defects in the jaw region and to a method for producing such an implant. More particularly, the invention relates to an implant which is placed over a defect site filled with a bone substitute material and over which the soft tissue is then closed.

BACKGROUND OF THE INVENTION

Implants for covering bone defects in the jaw region are known. There are available both bioresorbable implants that slowly dissolve after placement, and implants that either remain in the body or need to be removed after a certain time.

A general overview of known implants for covering bone defects is given in the paper of Liu et al. "Mechanisms of Guided Bone Regeneration: A Review", The Open Dentistry Journal, 2014; 8: p. 56-65.

For example, non-resorbable PTFE membranes are available, which are easily placed, but need to be explanted.

Furthermore, in particular collagen membranes are available as a resorbable material.

The latter have the advantage that they do not need to be explanted, which however is associated with the drawback that they are not particularly dense, so that there is a risk for soft tissue to grow into the filled bone defect site or for bone material to escape from the defect site.

OBJECT OF THE INVENTION

Given the above, the invention is based on the object of mitigating the drawbacks of the prior art.

More particularly it is an object of the invention to provide a bioresorbable implant which can be placed easily and which reliably separates soft tissue from the bone material, in particular from the bone substitute material, in the initial phase after placement.

SUMMARY OF THE INVENTION

The object of the invention is already achieved by an implant for covering bone defects in the jaw region and by a method for producing an implant for covering bone defects in the jaw region according to any one of the independent claims.

Preferred embodiments and modifications of the invention are specified by the subject matter of the respective dependent claims.

The invention relates to an implant for covering bone defects in the jaw region, which comprises a magnesium film.

Magnesium film refers to a film made of magnesium or a magnesium alloy, which predominantly consists of magnesium, i.e. contains more than 50% of magnesium (unless otherwise stated, percentages mean percent by weight throughout the present description).

Surprisingly, it has been found that such a magnesium film permits to achieve a clear separation between soft tissue and the defect site which is in particular filled with a bone substitute material, such as in particular homologous or autologous bone grafts.

The bioresorbable properties of magnesium as such are known. However, it is quite surprising that merely a film in the jaw region is capable of resisting a corrosive attack for a time period sufficient for completion of the growth of natural bone tissue into the defect site to a degree so that an ingrowth of soft tissue is prevented until the implant decomposes at least partially.

The invention is suitable for all types of treatment of bone defects in the jaw region, in particular also for sinus lift corrections.

Bone substitute material that is employed includes in particular materials containing calcium carbonate phosphate or hydroxyapatite. This may be both synthetic and natural material, in particular material produced from donor bones of human or porcine origin, for example. The bone substitute material may be placed in the form of a granulate as well as in the form of an adapted shaped body approximately conformed to the contour of the defect site, at least in sections thereof.

The implant is preferably geometrically stable. This means that an implant that has been bent will not change its shape due to its own weight, for example.

For this purpose, in particular a magnesium film with a thickness between 50 and 300 µm, preferably between 70 and 200 µm is used.

The implant preferably has a curved shape. Thus, it can be placed on the defect site and may even be clamped on the jaw ridge, at best.

In particular, a radius of curvature from 0.5 to 10 cm, preferably from 0.7 to 1.5 cm is provided, at least in sections thereof.

It has been found that a magnesium film of the thickness mentioned above can be bent in particular about an angle of >30°. This angle is defined by the angle enclosed by the tangents to longitudinal edge portions of the implant. It is in particular contemplated that the longitudinal edge portions of the implant lie in parallel to each other or even enclose an angle of more than 180° in order to fix, in particular to clamp the implant.

In a further embodiment of the invention, the implant has at least one recess for a tooth. Preferably, a front and/or rear end of the implant is recessed so that the adjacent sides partially surround the tooth. On the one hand, this facilitates the placement, on the other hand the risk of ingrowth of soft tissue is further reduced.

The implant preferably has a size of 0.5 to 25 cm². If a recess for a tooth is provided, it preferably takes up an area of more than 0.25 cm².

According to a further embodiment of the invention, the implant has a coated and/or etched surface.

It has been found that in particular an implant that has been immersed in an acid exhibits improved properties with respect to optional bending radii and corrosion properties.

The implant furthermore preferably has a smooth surface with an average roughness $R_a$ of less than 0.08, preferably less than 0.03, and most preferably less than 0.02 µm. Such a smooth surface may in particular be achieved by an acid treatment, for example with nitric acid.

In particular etching and/or passivation is suggested as a surface treatment. It has proved to be particularly suitable for a pre-cleaned implant, in particular an implant pre-cleaned with acid, to be immersed in hydrofluoric acid for at least 10 minutes, whereby a protective layer of magnesium fluoride is formed by agitated immersion. The passivated surface, in particular the magnesium fluoride layer, preferably has a thickness of less than 5 µm, more preferably less than 2 µm.

It is in particular suggested to produce a layer with a thickness between 0.2 and 2 μm, preferably between 0.7 and 1.5 μm.

In this manner, a well interlinked and preferably pore-free, scratch-resistant layer is formed which does not tend to crack even in the case of narrow bending radii.

The film preferably has no openings, at least in a central area thereof, that is in particular in the area which is arranged directly above the defect site. This ensures tight sealing of the defect.

In a further embodiment of the invention, the implant is structured and/or perforated in sections thereof, in particular along a peripheral area thereof. In particular by perforation, for example in the form of a mesh-like structure, or by structuring, in particular pleating, it is possible to provide for a better bending of the implant and/or to improve adhesion thereof to the adjacent tissue.

The implant is preferably made of pure magnesium (purity of more than 99%) or of a magnesium alloy which may comprise from 1 to 6% of yttrium, from 0.5 to 3% of zinc, from 0.1 to 2% of calcium, and/or from 0.6 to 1.5% of manganese. However, the magnesium film preferably includes less than 500 ppm of iron, copper, and/or nickel.

The invention furthermore relates to a kit for covering bone defects in the jaw region, which comprises an implant as described above and pins for fixing the implant in the jaw. Pins in the sense of the invention are to be understood in particular as comprising pins, nails, or screws. The pins are also preferably made of magnesium or a magnesium alloy.

As contemplated according to a further embodiment of the invention, the implant may have bores through which the pins are introduced. However, it is likewise conceivable to introduce the fixing bore with the pin itself, in particular if the latter has a tip.

The invention furthermore relates to a method for producing an implant, in particular an implant as described above, which is designed for covering bone defects in the jaw region.

According to the invention, a magnesium film is provided. The magnesium film is shortened to the length of a site to be covered, and the magnesium film is bent.

The bending of the magnesium film is preferably accomplished using a mold or by means of a bending tool so as to reduce the risk for kinks and edges.

In order to shorten the implant to the desired length and/or to introduce recesses, for instance for a tooth, the implant can be cut or punched, for example.

In order to form a layer, the magnesium film is preferably treated with hydrofluoric acid, in particular over a period of more than 10 hours, preferably more than 12 hours, and in particular with a hydrofluoric acid of a concentration of more than 30%.

The invention furthermore relates to a method for cosmetic and/or surgical jaw reconstruction, which method comprises placing the implant as described above over a defect site that has been filled in particular with a bone substitute material, and closing the soft tissue over the defect site, in particular by suturing.

It has been found that the magnesium film of the invention allows, in a straightforward way, to provide a bioresorbable implant which largely prevents ingrowth of soft tissue during the formation of natural bone material.

The implant does not need to be removed, rather it decomposes. Surprisingly, in spite of the relatively large surface area of the employed film that is used, there is no undesirably high degree of bubble creating gas formation resulting.

Once natural bone tissue has formed, it is then possible to introduce a dental pin implant into the former defect site, for example. The dental pin implant can already be introduced before the magnesium film has decomposed.

The implant according to the invention is particularly suitable for the following optional applications:

First, implants in the form of a magnesium film can be employed for treating injuries to the Schneiderian membrane.

The Schneiderian membrane separates the jaw bone from the maxillary sinus, and injury thereof entails an extreme risk of infection.

It has been found that such a defect site can be closed by inserting a thin magnesium film. Presumable due to an increase in the pH value, the magnesium appears to have an anti-inflammatory effect and moreover accelerates the formation of natural bone tissue, for example if bone filling material is used.

Another possible application is the prevention of wound dehiscences which are common with conventional membranes, such as PTFE membranes.

Moreover, the latter materials need to be removed in a further surgery.

It has been found that suture dehiscences over a magnesium film spontaneously lead to complete wound closure.

In this way, defects of up to 10 mm can be tolerated without causing infections.

Surprisingly, the film corrodes quite slowly and remains mechanically stable over a long period of time.

Furthermore, it is possible to remediate defect sites in the jaw.

In particular, a magnesium film below a periosteal flap is capable of autonomously causing regeneration of the cortical wall. Treatment for regeneration of the cortical wall is possible in any area thereof, in particular of the lateral cortical wall.

Under defect sites such as the exposed area of a pin implant, for example, a cortical wall will form around the defect site.

Finally, magnesium films may as well be used preventively for initial post-surgical infection protection.

Furthermore, because of their geometrical stability, the implants of the invention are suitable for shaping complex, three-dimensional bone regenerates.

For this purpose, the filling material is introduced into the defect site below the magnesium film.

Due to its three-dimensional geometrically stable free-form surface, the magnesium film preserves this shape until bony consolidation and then dissolves completely.

BRIEF DESCRIPTION OF THE DRAWINGS

The subject matter of the invention will now be explained in more detail by way of exemplary embodiments with reference to the drawings of FIGS. 1 to 8.

DETAILED DESCRIPTION OF THE DRAWINGS

Figure 1:
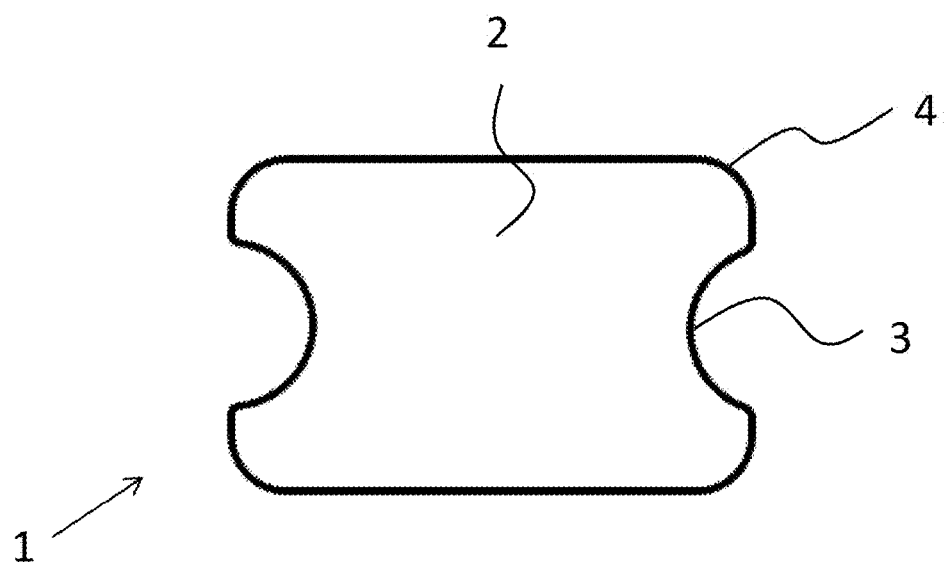
FIG. 1 shows an exemplary embodiment of an implant 1 for covering bone defects in the jaw region.

FIG. 1 shows a first exemplary embodiment of an implant for covering bone defects in the jaw region.

In this exemplary embodiment, the implant 1 consists of a magnesium film 2 of a thickness from 50 to 150 μm, which is in particular made of a magnesium alloy. Implant 1 has rounded corners, and in this exemplary embodiment it has two recesses 3 which are intended for an adjacent tooth.

Thus, the implant is in particular designed for covering a defect site in the jaw, where one tooth or several teeth are missing.

Figure 2:
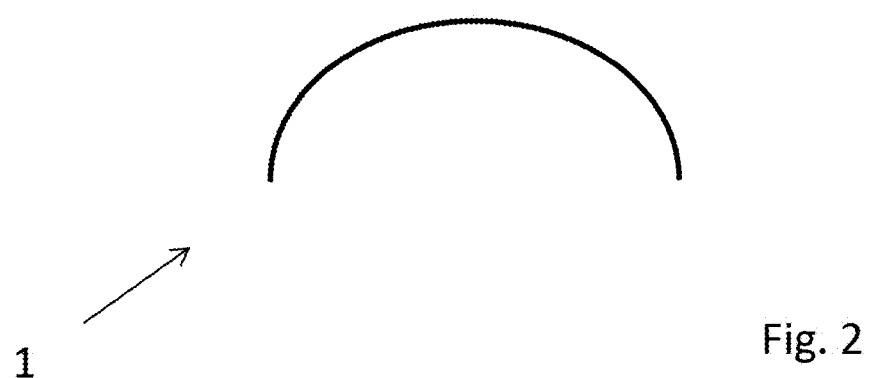
FIG. 2 shows a side view of the implant.

FIG. 2 shows a side view looking towards the recess (3 in FIG. 1) of the implant 1 illustrated in FIG. 1.

It can be seen that the implant is curved. In this exemplary embodiment, the longitudinal edge portions of the implant are almost opposed to each other, so that the implant can be fixed on a jaw ridge, in particular clamped or clipped thereon.

Figure 3:
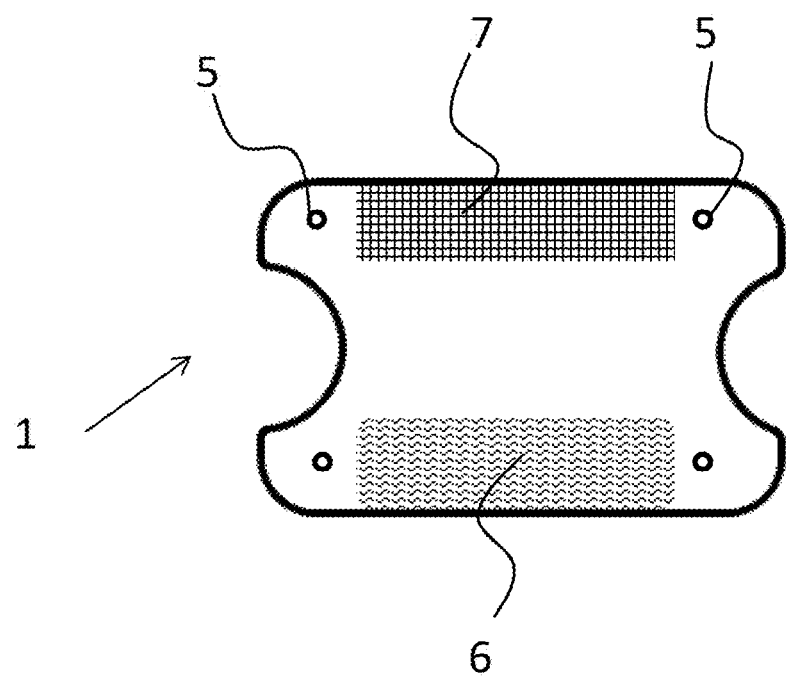
FIG. 3 shows another embodiment of an implant.

FIG. 3 shows another embodiment of an implant 1.

On the one hand, the implant 1 has bores 5 which are used to introduce sutures, pins, screws, or nails.

In this exemplary embodiment the implant 1 furthermore has a mesh-like area 7, that is to say an area with perforations. These perforations may serve to facilitate the bending or for improved adhesion to the tissue.

Furthermore, a structured area 6 is also shown, which may in particular be in the form of a pleating and serves to conform the implant 1 to the jaw bone.

Figure 4:
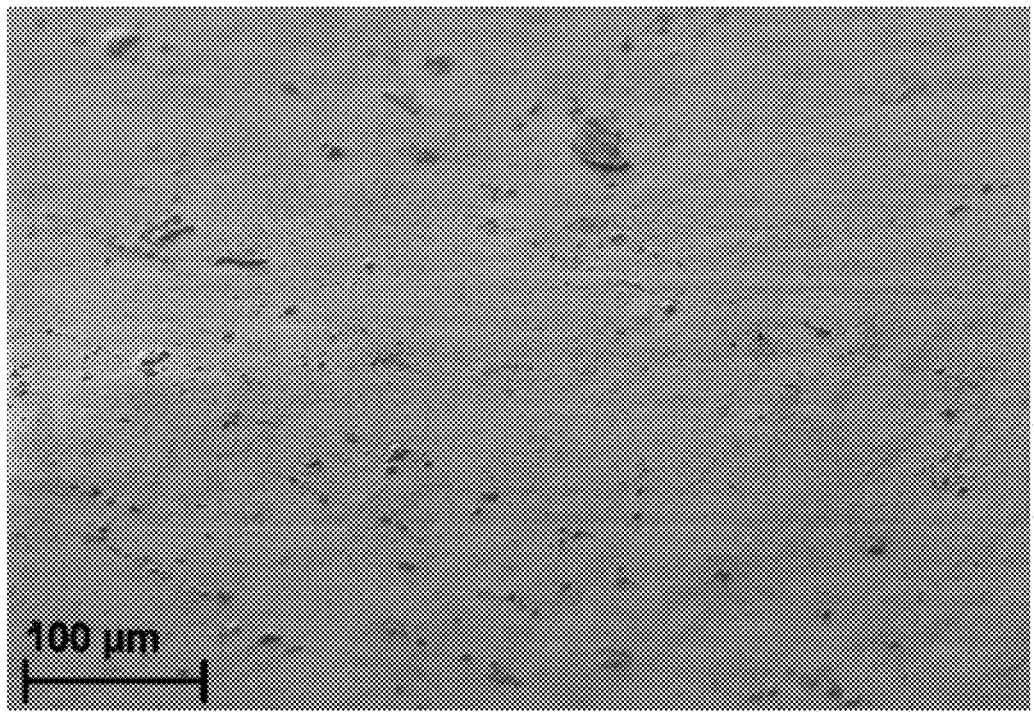
FIGS. 4 to 6 are raster electron micrographs of an implant.

FIG. 4 shows a scanning electron micrograph of the surface of an implant, for which a magnesium film was provided with a magnesium fluoride layer by immersion into hydrofluoric acid.

The result is a smooth scratch-resistant thin layer of approximately 1 μm thickness, which allows for even rather narrow bending radii.

Figure 5:
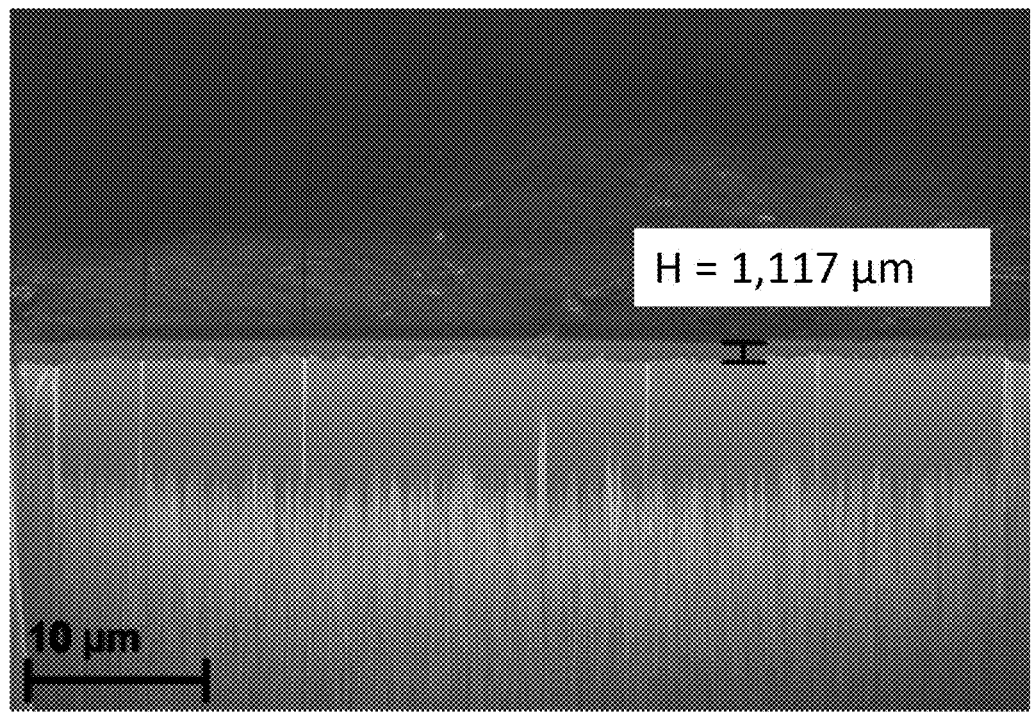

FIG. 5 also shows a scanning electron micrograph, in this case of a section of the film, in which the magnesium fluoride layer is already clearly discernible.

Figure 6:
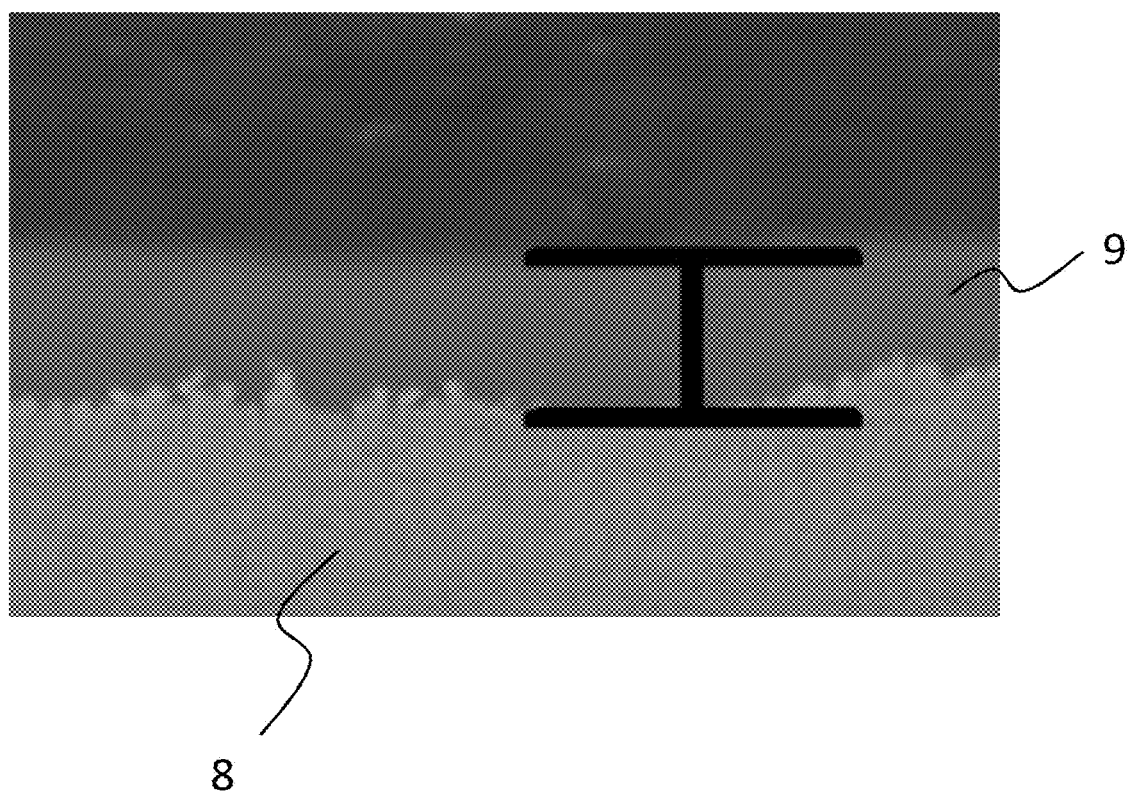

FIG. 6 is a view of a detail of FIG. 5.

The thin magnesium fluoride layer 9 formed on the magnesium layer 8 can be seen.

It is readily apparent that the magnesium fluoride layer 9 is well interlocked with the underlying magnesium layer, which is probably the cause for the good adhesion of the layer, inter alia.

Figure 7:
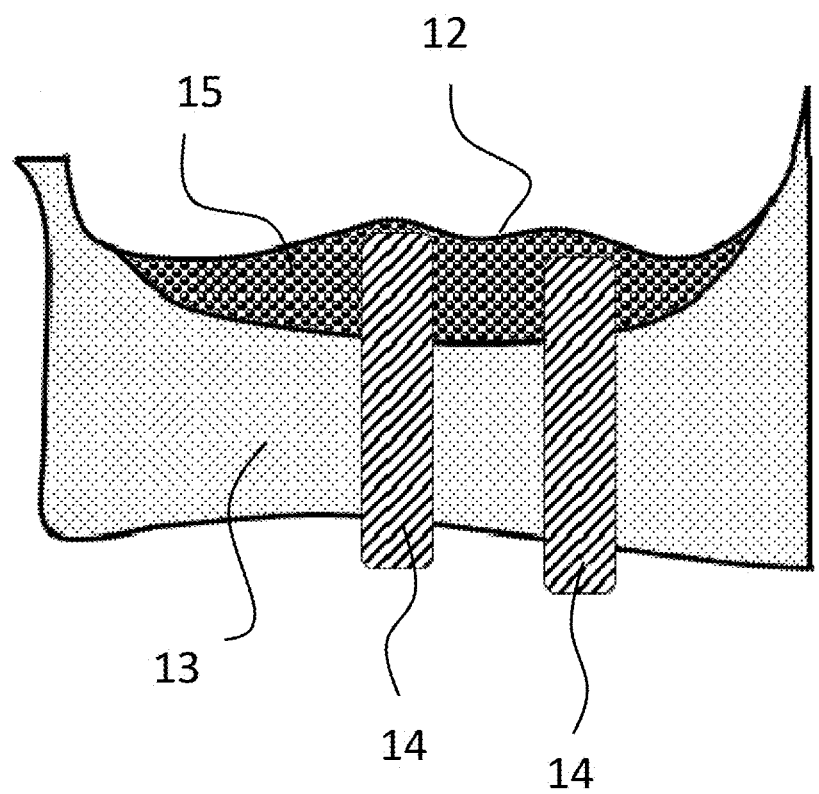
FIG. 7 schematically illustrates the use of an implant according to the invention for the prevention or treatment of injuries to the Schneiderian membrane.

FIG. 7 schematically illustrates a first possible application of the implant according to the invention.

The implant of the invention in the form of a magnesium film can be employed for the treatment of injured Schneiderian membranes.

In particular when pin implants 14 are placed, as illustrated here, which serve to receive a dental implant, injury may occur to the Schneiderian membrane 12 which separates the maxillary bone 13 from the maxillary sinus.

In many cases, as illustrated here, an interspace between the jaw bone 13 and the Schneiderian membrane 12 is filled with a bone substitute material, in particular a calcium phosphate granulate, in order to increase the thickness of the receding jaw bone so that the implant 14 can be placed.

Injury to the Schneiderian membrane 12 is accompanied by an extremely high risk of infection. If, during surgery, such an injury is detected, the surgical procedure is usually interrupted, and only after a healing period of several months the pin implant 14 is again tried to be placed.

It has been found that this can be avoided by using an implant according to the invention in the form of a magnesium film which closes the Schneiderian membrane 12.

For example, in case of a defect the magnesium film can be introduced either through the bores for the pin implants 14 or through a lateral opening of the jaw ridge 13.

It will be understood that if the magnesium film is introduced through the bores for the pin implants, it can be rolled up previously, for example.

The Schneiderian membrane 12 is sealed by the magnesium film. Surprisingly, already a thin magnesium film of at least 50 μm provides sufficient sealing without decomposing within a very short period of time as would actually be expected.

Thus, the magnesium film can therefore allow to immediately continue the surgical procedure and moreover offers the advantage that the magnesium film, in particular if it is sufficiently thick, provides a good backing for the bone material used. The growth of natural bone tissue is also promoted by the magnesium film.

It will be understood, however, that the magnesium film may as well be used preventively, without an injury to the Schneiderian membrane.

Figure 8:
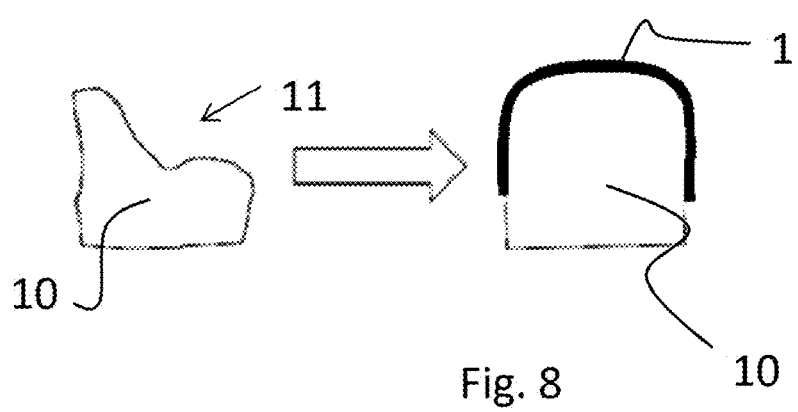
FIG. 8 schematically illustrates the use of an implant according to the invention for so-called "lateral augmentation" (reconstruction of the jaw bone).

FIG. 8 schematically illustrates the use of an implant 1 according to the invention for a three-dimensional reconstruction of defect sites in the jaw bone.

A jaw bone 10 which has a defect site 11 is covered with a bent implant 1 consisting of a magnesium film. The implant 1 defines a three-dimensional free-form surface.

As can be seen in the figure on the right, the bone tissue of the jaw ridge 10 that is being formed follows this free-form surface and forms a rounded jaw ridge which approximates the natural shape. This approximation will in particular usually be better than when using inserted bone blocks of donor material.

The invention permits to provide, in a straightforward way, a resorbable implant for covering bone defects in the jaw region.

LIST OF REFERENCE NUMERALS

1 Implant
2 Magnesium film
3 Recess
4 Corner
5 Bore
6 Structured area
7 Mesh-like area
8 Magnesium layer
9 Magnesium fluoride layer
10 Jaw ridge
11 Defect site
12 Schneiderian membrane
13 Jaw bone
14 Pin implant
15 Filler material

The invention claimed is:
1. A method for cosmetic or surgical jaw reconstruction, comprising the steps of:
providing an implant consisting of pure magnesium having a purity of more than 99%, the implant being in the form of a film having a central area without openings and a thickness between 70 and 200 μm, cutting the implant to a size appropriate for covering a defect site in a jaw region to be covered, bending the implant into a curved shape, placing the implant over the defect site in the jaw region such that the central area without openings is arranged directly above the defect site and seals the defect, immovably fixing the implant in the jaw with at least one fastener in a fixed position at the time of placing the implant over the defect site, closing soft tissue over the implant, and leaving the implant to decompose in the fixed position.

2. The method of claim 1, wherein the implant contains less than 500 ppm of iron, copper or nickel.

3. The method of claim 1, wherein prior to the placing of the implant, further comprising the step of filling the defect site with a bone substitute material or bone graft.

4. The method of claim 1, wherein the at least one fastener comprises a pin, a screw, or a suture.

5. The method of claim 1, wherein the step of cutting the implant to a size comprises providing at least one recess for a tooth in an edge of the implant.

6. The method of claim 1, wherein the step of bending the implant into a curved shape comprises bending the implant so as to form a radius of curvature between 0.5 and 10 cm.

7. The method of claim 6, wherein the implant is bent so as to form a radius of curvature between 0.7 and 1.5 cm.

8. The method of claim 6, wherein the step of bending the implant into a curved shape comprises bending the implant about an angle of greater than 30°.

9. The method of claim 1, wherein prior to the step of bending the implant, further comprising the step of subjecting the implant to a surface treatment comprising etching, coating, or passivating.

10. The method of claim 1, wherein prior to the step of bending the implant, further comprising the step of structuring the implant along peripheral areas thereof.

11. The method of claim 10, wherein the structuring comprises producing at least one of bores, perforations, a mesh-like structure, and a pleated structure along peripheral areas of the implant.

12. The method of claim 1, wherein the defect site in the jaw region includes a jaw bone defect or a Schneiderian membrane defect.

13. The method of claim 1, wherein immovably fixing the implant in the jaw comprises fixing the implant on a jaw ridge.

14. The method of claim 1, wherein immovably fixing the implant in the jaw comprises introducing sutures, pins, screws, or nails through bores which are arranged on longitudinal edge portions of the implant.

15. The method of claim 1, further comprising:

waiting for natural bone tissue to form at the defect site under the implant; and introducing a dental pin into the natural bone tissue.

16. The method of claim 15, wherein introducing the dental pin into the natural bone tissue is performed before the implant has decomposed.

17. The method of claim 1, wherein the implant has a smooth surface with an average roughness of less than 0.08 μm.

18. The method of claim 1, wherein the implant has a smooth surface with an average roughness of less than 0.03 μm.

19. The method of claim 1, wherein sealing the defect includes sealing the Schneiderian membrane.

* * * * *